(12) United States Patent
Bonnefous

(10) Patent No.: US 7,347,820 B2
(45) Date of Patent: Mar. 25, 2008

(54) PHASED ARRAY ACOUSTIC SYSTEM FOR 3D IMAGING OF MOVING PARTS

(75) Inventor: Odile Bonnefous, Rueil-Malmaison (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 444 days.

(21) Appl. No.: 10/533,029

(22) PCT Filed: Oct. 31, 2003

(86) PCT No.: PCT/IB03/04899

§ 371 (c)(1),
(2), (4) Date: Apr. 26, 2005

(87) PCT Pub. No.: WO2004/042424

PCT Pub. Date: May 21, 2004

(65) Prior Publication Data

US 2006/0074309 A1    Apr. 6, 2006

(30) Foreign Application Priority Data

Nov. 6, 2002    (EP) ................................ 02292768

(51) Int. Cl.
*A61B 8/00* (2006.01)
(52) U.S. Cl. ..................................... 600/437
(58) Field of Classification Search ................ 600/437, 600/440–441, 443, 447, 450, 453–456; 367/93–94, 367/103–105; 382/107, 285, 294; 73/625, 73/626; 128/916
See application file for complete search history.

(56) References Cited

U.S. PATENT DOCUMENTS 4,067,236 A  *  1/1978  Hottinger ................. 73/861.25

(Continued)

FOREIGN PATENT DOCUMENTS

WO    WO 0146713 A1    6/2001

(Continued)

OTHER PUBLICATIONS

Lockwood, G.R., et al., "Real-Time 3-D Ultrasound Imaging Using Sparse ☐☐Synthetic Aperture Beamforming", IEEE Transactions on Ultrasonics, Ferroelectrics, and Frequency Control, Jul. 1998, vol. 45, No. 4, 980-988. ☐☐.*

(Continued)

*Primary Examiner*—Salieu M. Abraham
(74) *Attorney, Agent, or Firm*—Tony Piotrowski

(57) ABSTRACT

The invention relates to an ultrasound phased array imaging system comprising: probe (10) with a 2-D array of transducer elements (12) for acquiring 3-D ultrasound data of a volume of a body, including moving tissue and fluid flow; a beamforming system (10, 12, 14, 16) for emitting and receiving in real time ultrasound beams in said volume, which provides, in real time and in 3-D, more than one spatial receive beams signals for each transmission beam within an ensemble length of more than two temporal samples, among which the receive flow beam signals and the receive tissue beam signals are substantially temporally uncorrelated but spatially correlated; separation means (30) for processing in real time the receive beams signals, comprising adaptive spatial tissue filtering means using simultaneously more than one spatial receive beam signals acquired in 3-D within the ensemble length of more than two temporal samples, which separation means analyzes temporal variations of the respective successive receive signals and extracts flow receive beam signals from spatial combinations of receive beam signals; processing means (40, 50) and display means (62, 60) for processing flow Doppler signals and for displaying images based on said processed flow Doppler signals.

12 Claims, 4 Drawing Sheets

U.S. PATENT DOCUMENTS

| | | | |
|---|---|---|---|
| 4,103,679 A * | 8/1978 | Aronson | 600/456 |
| 4,265,126 A * | 5/1981 | Papadofrangakis et al. | 73/861.25 |
| 4,612,937 A * | 9/1986 | Miller | 600/441 |
| 4,790,322 A * | 12/1988 | Iinuma | 600/456 |
| 5,197,477 A * | 3/1993 | Peterson et al. | 600/454 |
| 5,257,629 A * | 11/1993 | Kitney et al. | 600/463 |
| 5,262,785 A * | 11/1993 | Silverstein et al. | 342/162 |
| 5,322,067 A * | 6/1994 | Prater et al. | 600/443 |
| 5,357,964 A * | 10/1994 | Spivey et al. | 600/455 |
| 5,386,830 A * | 2/1995 | Powers et al. | 600/455 |
| 5,443,071 A * | 8/1995 | Banjanin et al. | 600/455 |
| 5,454,371 A * | 10/1995 | Fenster et al. | 600/443 |
| 5,471,990 A * | 12/1995 | Thirsk | 600/455 |
| 5,474,073 A * | 12/1995 | Schwartz et al. | 600/456 |
| 5,485,842 A * | 1/1996 | Quistgaard | 600/443 |
| 5,546,807 A | 8/1996 | Oxaal et al. | |
| 5,570,691 A * | 11/1996 | Wright et al. | 600/447 |
| 5,623,930 A * | 4/1997 | Wright et al. | 600/456 |
| 5,675,554 A * | 10/1997 | Cole et al. | 367/138 |
| 5,678,554 A * | 10/1997 | Hossack et al. | 600/459 |
| 5,720,291 A * | 2/1998 | Schwartz | 600/456 |
| 5,724,976 A * | 3/1998 | Mine et al. | 600/459 |
| 5,876,345 A * | 3/1999 | Eaton et al. | 600/466 |
| 5,928,151 A * | 7/1999 | Hossack et al. | 600/443 |
| 5,980,458 A * | 11/1999 | Clark | 600/437 |
| 5,993,390 A | 11/1999 | Savord et al. | |
| 6,171,248 B1 * | 1/2001 | Hossack et al. | 600/459 |
| 6,213,947 B1 * | 4/2001 | Phillips | 600/443 |
| 6,241,675 B1 * | 6/2001 | Smith et al. | 600/443 |
| 6,245,017 B1 * | 6/2001 | Hashimoto et al. | 600/447 |
| 6,283,918 B1 * | 9/2001 | Kanda et al. | 600/441 |
| 6,322,511 B1 * | 11/2001 | Guracar et al. | 600/453 |
| 6,374,674 B1 * | 4/2002 | Mine | 73/606 |
| 6,383,139 B1 * | 5/2002 | Hwang et al. | 600/441 |
| 6,390,980 B1 * | 5/2002 | Peterson et al. | 600/443 |
| 6,425,868 B1 * | 7/2002 | Tamura | 600/454 |
| 6,458,082 B1 * | 10/2002 | Jackson et al. | 600/441 |
| 6,468,216 B1 | 10/2002 | Powers et al. | |
| 6,530,885 B1 * | 3/2003 | Entrekin et al. | 600/437 |
| 6,572,548 B2 * | 6/2003 | Cerofolini | 600/443 |
| 6,623,432 B2 | 9/2003 | Powers et al. | |
| 6,682,483 B1 * | 1/2004 | Abend et al. | 600/437 |
| 6,685,641 B2 * | 2/2004 | Liu | 600/443 |
| 6,709,394 B2 | 3/2004 | Frisa et al. | |
| 6,780,155 B2 * | 8/2004 | Li | 600/454 |
| 6,918,876 B1 * | 7/2005 | Kamiyama | 600/447 |
| 7,171,255 B2 * | 1/2007 | Holupka et al. | 600/427 |
| 7,201,715 B2 * | 4/2007 | Burdette et al. | 600/3 |
| 2001/0017937 A1 | 8/2001 | Bonnefous | |
| 2002/0010398 A1 | 1/2002 | Bonnefous | |
| 2003/0158477 A1 * | 8/2003 | Panescu | 600/424 |
| 2005/0053305 A1 * | 3/2005 | Li et al. | 382/260 |

FOREIGN PATENT DOCUMENTS

WO    WO 0147421 A1    7/2001

OTHER PUBLICATIONS

Lockwood, G.R., et al., "Real-Time 3-D Ultrasound Imaging Using Sparse Synthetic Aperture Beamforming", IEEE Transactions on Ultrasonics, Ferroelectrics, and Frequency Control, Jul. 1998, vol. 45, No. 4, 980-988.*

Nitta, N., et al. "Experimental Investigation of 3-D Blood Flow Velocity Measurement," Japanese Journal of Applied Physics, Publication Office of Japanese Journal of Applied Physics, Tokyo, Japan, vol. 35, No. 5B, May 1, 1996, pp. 3126-3130.

* cited by examiner

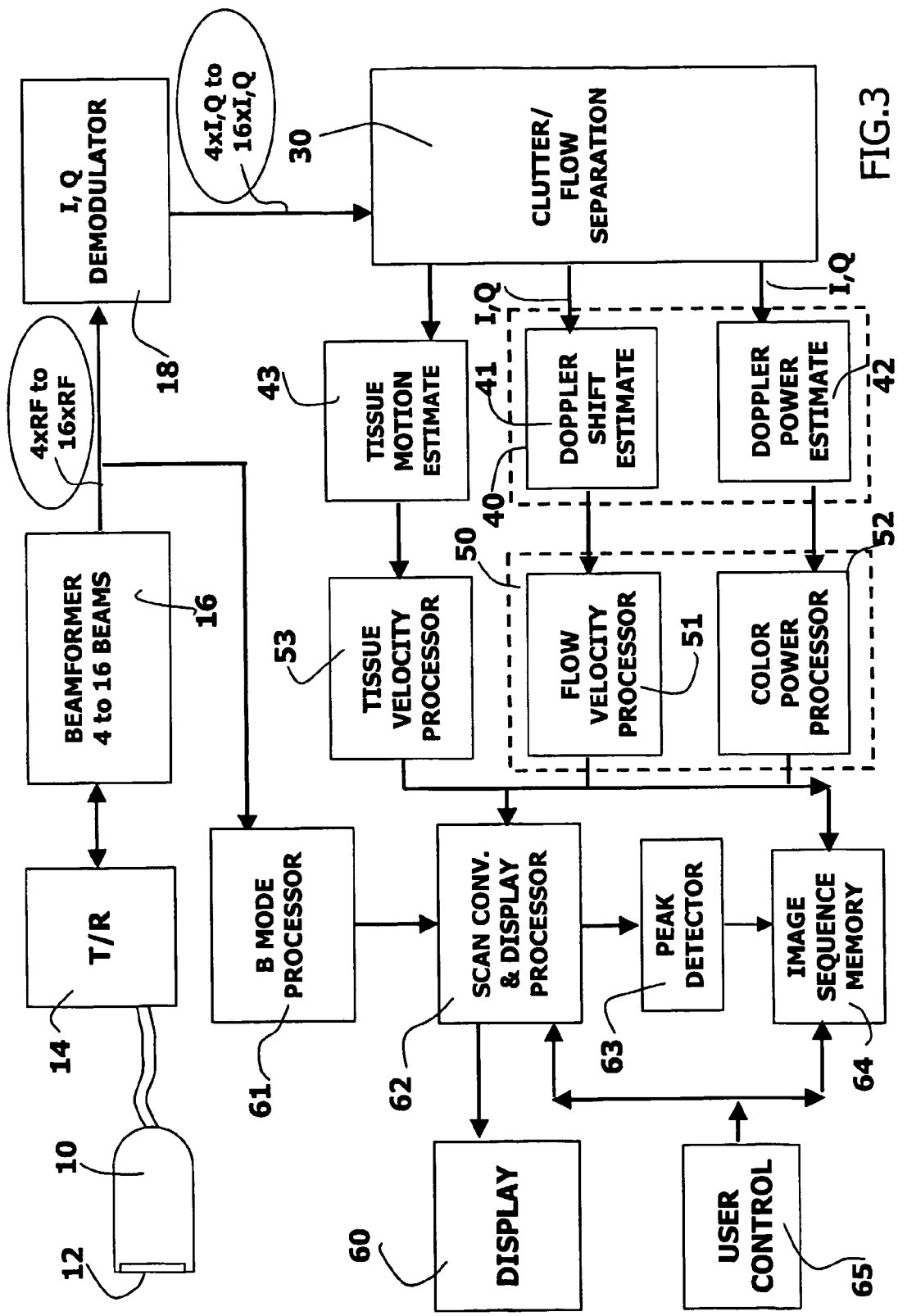

PHASED ARRAY ACOUSTIC SYSTEM FOR 3D IMAGING OF MOVING PARTS

FIELD OF THE INVENTION

The invention relates to an ultrasound, phased array imaging system and more particularly, to an imaging system, which uses an ultrasound transducer array with a 2D arrangement of transducer elements, having means to form 3-D motion images of moving parts of a body. These moving parts are typically blood flows and moving tissues like arterial or cardiac walls.

The invention particularly finds applications in the field of medical ultrasound imaging.

BACKGROUND OF THE INVENTION

Various methods and devices have been proposed for ultrasonically scanning a volume within a subject for three-dimensional imaging and display. Many of these techniques involve the scanning of a number of spatially adjacent image planes of a region of the body. The ultrasonic information from these associated planes can be analyzed and displayed on the basis of spatial coordinates of the data within a plane, and on the basis of the spatial relationship of each plane to the others. The information can be displayed in a three-dimensional image format such as a perspective view of the volume being imaged. A number of scanning techniques utilizing specially devised scanning devices have been proposed for acquiring these spatially related image planes. It is preferable, however, to be able to acquire information data for three-dimensional presentation without the need for special scanning devices or apparatus.

It has therefore been proposed to use ultrasound phased array imaging systems comprising a transducer array probe with transducer elements disposed in a 2-D plane for forming 3-D images of a region of a body. These known systems can provide real time 3-D gray images by acquiring data in a pyramidal volume whose boundaries lean onto the 2-D phased array perimeter and form angles of about 30°×30°. These 3-D images permit of examining in real time a body structure comprised in this pyramidal volume. In fact, these 3-D gray images are realized in real time with a frame rate of about 20 Hz. These 3-D gray images correspond to the reference volume scanned by the 2-D phased array probe where beam formation steps are performed at the level of the probe, allowing the synthesis of four simultaneous receive beams. Doing motion extraction in three dimensions and in real time presents additional problems to solve.

Now, conventional 2-D imaging systems for providing real time Doppler images of moving parts of a body are already known. Using said 2-D imaging systems, Doppler imaging requires analyzing typically eight successive transmit-receive signals in order to extract and process flow signals. With the 3-D systems previously described, real time 3-D flow imaging would necessitate an acquisition time that would be eight times longer than the time necessary to acquire 3-D gray images of a structure, achieving a frame rate of about 2 Hz. Another solution for acquiring real time 3-D Doppler flow images would be to acquire a volume eight times smaller than the pyramidal reference volume during one cardiac cycle. In this case, eight successive triggered cardiac cycles would be necessary to reconstruct the reference pyramidal volume. Hence, the known systems do not permit to form 3-D Doppler images of fluid flow or tissue motion of a body in real time because this operation would necessitate multiplying the acquisition time by eight in such a reference volume or would necessitate scanning a volume eight times smaller. In each case, the real time quality of such 3-D images would be unsatisfactory.

Because flow imaging allows to image coronary trees or vessels of organs such as liver and kidneys, etc., it is crucial to provide means that allow extending ultrasound modality to 3-D Doppler flow imaging in real time.

Ultrasonic images are subject to image artifacts arising from a number of sources such as reverberation, multipath echoes, and coherent wave interference. These artifacts will manifest themselves in various ways in the images, which can be broadly described as image tissue. The image tissue becomes particularly troublesome when images are presented in a three-dimensional format, as the three-dimensional tissue can interfere with a region of the body and obscure said region, which the clinician is attempting to visualize. Moreover, strong anatomic structures like arterial walls or cardiac walls mask the weak signals generated by blood. When imaging blood flow, these structures represent the tissue. Accordingly, it would be desirable to provide ultrasonic image information in a format in which tissue does not significantly impair the images of the body region. For example, it would be desirable to provide ultrasonic image information in a format in which tissue information may be separated from flow information.

It is already known to image the body using Doppler information. Doppler information has been used to image the body in two distinct ways. One Doppler imaging technique is commonly referred to as Doppler velocity imaging. As is well known, this technique involves the acquisition of Doppler data at different locations called sample volumes over the image plane of an ultrasonic image. The Doppler data is acquired over time and used to estimate the Doppler phase shift or frequency at each discrete sample volume. The Doppler phase shift or frequency corresponds to the velocity of tissue motion or fluid flow within the body, with the polarity of the shift indicating direction of motion or flow. This information may be color coded in accordance with the magnitude of the shift or velocity and its polarity, and usually overlaid over a structural image of the tissue in the image plane to define the structure of the moving organs or flowing fluids. The colors in the image can provide an indication of the speed of blood flow and its direction in the heart and blood vessels, for instance.

A second Doppler technique is known as power Doppler. This technique is unconcerned with estimations of the velocity of motion or fluid flow. Rather, it focuses simply on the intensity of the received signals that exhibit a Doppler shift. This Doppler signal intensity can be measured at each sample volume and displayed in a color variation. Unlike Doppler velocity imaging, power Doppler does not present the problems of directionality determination and low sensitivity that are characteristic of velocity imaging. Color power Doppler simply displays the Doppler signal intensity at a sample volume in a coded color. Like color Doppler velocity imaging, the color power Doppler display is conventionally displayed with a structural B mode image to define the organ or tissue structure in which motion is occurring. Since the value at each sample volume can be averaged over time or based upon a peak value, and is not subject to the constant changes of velocity and direction which are characteristic of Doppler velocity signals, the color power Doppler display can be presented as a stable display of motion or flow conditions in the body.

SUMMARY OF THE INVENTION

It is an object of the invention to provide an ultrasound phased array imaging system comprising a transducer array with transducer elements disposed in a 2-D arrangement for forming ultrasound 3-D Doppler images in real time, such as Doppler velocity images or Doppler power images in real time. The system of the invention provides said ultrasound 3-D Doppler velocity images or Doppler power images in real time by acquiring data in a pyramidal volume, called reference volume, whose boundaries lean onto the 2-D phased array perimeter of the 2-D arrangement and form angles of about 30°×30° or more.

The systems described as prior art do not permit to form 3-D Doppler images of a fluid flow of a body in real time in the volume called volume of reference, because this operation would necessitate multiplying the acquisition time by eight with respect to the acquisition time for forming 3-D gray images. These systems would only permit of forming 3-D Doppler images of a fluid flow of a body in real time in a volume eight times smaller than said volume of reference, which would again result in multiplying by eight the time necessary to reconstruct the 3-D image of the whole reference volume. The object of the invention is not only to propose an ultrasound system to form 3-D gray structural images in real time, or 2-D Doppler images in real time, but to propose an ultrasound system to acquire 3-D data and to form 3-D Doppler images of moving parts of a body in real time.

The ultrasound viewing system of the invention comprises means to minimize the acquisition time duration with respect to the known systems. The number of temporal samples, i.e. successive signals along a transmission beam, is defined as an "ensemble length". This system comprises means to reduce to 3 or 4 the number of successive signals out of the eight signals previously required. This operation reduces the acquisition time, possibly dividing the acquisition time by more than two. This system is able to provide four to sixteen reception beams for one emission beam, which multiplies by one to four the scanned volume at each transmission. Hence, The total acquisition time gain is then a factor of two to ten. The fact that few temporal samples are used is compensated by the fact that a larger number of spatial samples is available. A target receives an only emission beam and is examined using more than one received beams, for example four to sixteen received beams in parallel, which see this target differently, and with more than two temporal samples, for example three to four successive transmissions, which allows to analyze the temporal variations of the successive signals, due to the displacement of the target.

It is also an object of the present invention to provide means for separating tissue information signals from fluid flow information signals. According to the invention, this system has means for acquiring echo signals from this reference volume and forming complex data. This system has means for separating tissue complex data from flow complex data. This system has further first means for tissue motion estimation and second means for flow estimation. The system of the invention can provide on the one hand real time 3-D Doppler flow velocity images or real time Doppler power images from flow estimation, and it can provide on the other hand real time tissue velocity images from tissue estimation. A technique is further presented for acquiring in real time three-dimensional ultrasonic images using 2-D phased array transducer systems.

The invention can be applied to measure the motion rate of a moving part of the body, for instance the blood flow rate or tissue motion rate.

BRIEF DESCRIPTION OF THE DRAWINGS

The invention is described hereafter in detail in reference to the following diagrammatic drawings, wherein:

FIG. 3 shows a block diagram of an ultrasound apparatus comprising the system of FIG. 1.

DESCRIPTION OF THE PREFERRED EMBODIMENTS

Figure 1:
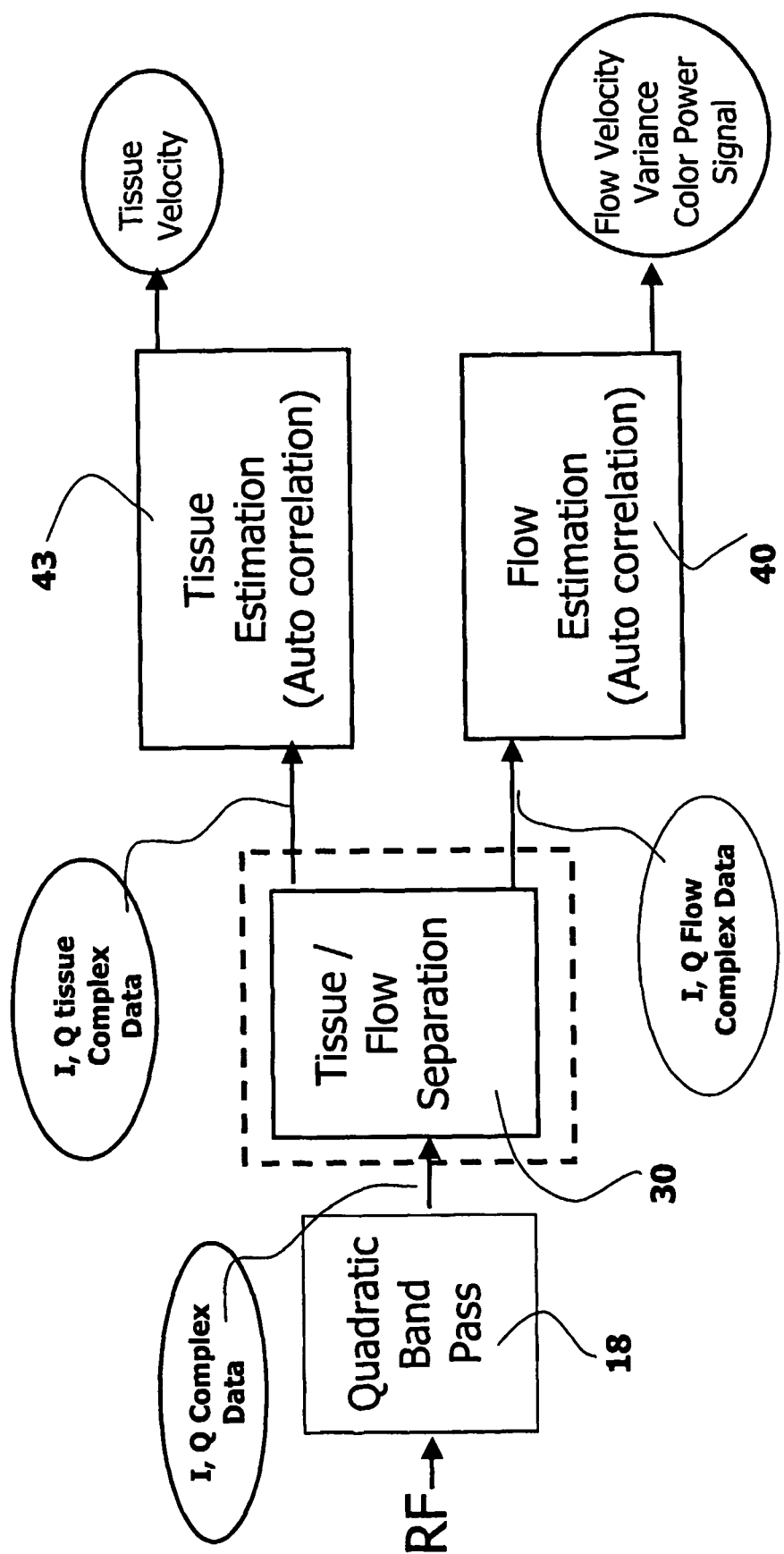
FIG. 1 represents a general block diagram of an ultrasonic imaging system constructed in accordance with the principles of the present invention.

The invention relates to an ultrasound, phased array imaging system and, more particularly, to an imaging system, which uses a transducer array with transducer elements in a 2-D arrangement. For example, the transducer elements are disposed in a 2-D arrangement in a 2-D plane. This ultrasound viewing system has means to form real time 3-D Doppler color images of moving parts of a body, for instance for imaging a fluid flow, such as a blood flow in a vessel or in the heart; or for imaging tissue motion such as heart walls.

This ultrasound viewing system has means to divide by two to ten the acquisition time duration with respect to conventional ultrasound systems. This ultrasound viewing system comprises means to multiply by four to sixteen the number of beams in the reception phase. Hence, said system provides more than one reception beams, for example four to sixteen reception beams for one emission beam, which multiplies by one to four a scanned volume at each transmission with respect to conventional ultrasound systems.

Besides, more than two temporal samples, for example only three or four or more successive signals out of eight signals are used to measure fluid flow or motion of a body part. This operation of using only said three or four or more successive signals again divides the acquisition time at least by eight to three. The fact that few temporal samples are available is compensated by the fact that a large number of spatial samples is available. The number of temporal samples is defined as "ensemble length", also called packet size, denoted by EL. Hence, it is an object of the invention to divide the number of temporal samples EL. A target receives an only emission beam and is examined using at least four and preferably sixteen received beams in parallel, which see this target differently, and with at least three or four successive transmissions, which allows analyzing the temporal variations of the successive signals, due to the displacement of the target.

The ultrasound viewing system of the invention has separation means to separate tissue information from flow information. Then, the ultrasound viewing system of the invention has further means to provide separately Doppler tissue velocity images and Doppler flow images or Doppler power images. A technique that is used in this separation means of this ultrasound imaging system is called hereafter "multiline data whitening".

The beams Doppler signals are unknown linear combinations of the Doppler echoes of a moving part, such as the echoes of fluid flow, and the Doppler echoes of tissue, these latter echoes being temporally uncorrelated, but spatially correlated. According to the invention, it is possible to extract flow Doppler signals using only an ensemble length of three, four or more temporal samples, from spatial combination of ultrasound signals. The invention provides means for ultrasound "signal whitening", which is applied to 3-D flow imaging, allowing the separation of flow signal from tissue signal. In the example of blood flow estimation, the tissue is constituted for instance by vessel walls, heart walls, valves, etc. A spatial correlation matrix is computed, and diagonalized allowing the separation of the uncorrelated Doppler components corresponding to flow and tissue signals. The Doppler flow signals are then processed classically with classical autocorrelation processing means to measure fluid velocity, for example blood velocity. The power of this signal can be used to provide 3-D angiograms or other cardiographic images.

Referring first to FIG. 3, a block diagram of an ultrasonic diagnostic imaging system constructed in accordance with the principles of the present invention is shown. An ultrasonic probe 10 includes a 2-D phased array transducer 12, which transmits waves of ultrasonic energy into the body of a patient and receives ultrasonic echoes returning from structures in the body. In the case of ultrasonic wave transmission for Doppler interrogation of the body, it is the echoes returning from moving tissue, or from blood and other fluids in the body that are of interest. The ultrasonic probe 10 is connected to a transmitter/receiver 14, which alternately pulses individual elements of the transducer to shape and steer an ultrasonic beam, and receives, amplifies and digitizes echo signals received by the transducer elements following each pulse transmission. The transmitter/receiver 14 is coupled to a beamformer 16, which controls the times of activation of specific elements of the transducer 12 by the transmitter/receiver 14. Circuits that are not represented, for performing transmitter/receiver functions and beamformer function, may be partially in the probe and partially outside the probe, thus forming a beamforming system 10, 12, 14, 16 in the imaging system. The timing of activation enables the transducer 12 to transmit a shaped and focused ultrasound beam in a desired direction. The beamformer 16 also receives the digitized echo signals produced by the transmitter/receiver during echo reception and appropriately delays and sums them to form coherent echo signals. The echo signals produced by the beamformer 16 are coupled to a B mode processor 61 and to the I,Q demodulator 18.

According to the invention, for each transmission beam, this beamforming system 10, 12, 14, 16 simultaneously forms in 3-D at least four to sixteen receive beams, or more, and respectively issues four to sixteen or more receive echo signals denoted by 4×RF to 16×RF.

The B mode processor 61 processes the amplitude information of the echo signals, denoted by RF, on a spatial basis for the formation of structural images of the tissue in the area of the patient being scanned. According to the invention, the I,Q demodulator 18 demodulates the four to sixteen, or more, received echo signals denoted by 4×RF to 16×RF into four to sixteen quadratic components, i.e. complex data, denoted by 4×I,Q to 16×I,Q, or more, for Doppler processing.

Referring to FIG. 1, which shows a block diagram of an ultrasound system for real time 3-D Doppler imaging according to the invention, the four to sixteen I,Q quadratic complex data, or more, issued by the I,Q demodulator 18, which are denoted by 4×I,Q to 16×I,Q, are processed by tissue/flow separation means 30 for separating 3-D tissue I,Q complex data from 3-D flow I,Q complex data. The separation is done using an adaptive spatial tissue filtering using simultaneously the four to sixteen beams acquired in 3-D. The tissue/flow separation processor 30 yields I,Q tissue complex data on the one hand and I,Q flow complex data on the other hand. The flow complex data are processed by flow estimation means 40 comprising autocorrelation means, which can yield flow velocity variance data or power data. The tissue I,Q complex data may be processed by tissue estimation means 43 comprising autocorrelation means, which can yield tissue velocity data. The tissue/flow separation processor 30 of the ultrasound imaging system of the invention processes the I,Q complex data in such a way that the resulting 3-D Doppler flow data are produced in real time.

Referring to FIG. 3, for producing flow velocity images, the flow estimation processor 40 comprises a Doppler shift estimation processor 41, which operates in a conventional manner to estimate a Doppler phase or frequency shift from the I,Q flow complex data at each sample volume location of the image field. The Doppler shift estimation processor 41 operates on a number of signal samples resulting from the interrogation of each sample volume location by an ensemble of Doppler interrogation pulses. The sample volume values are applied to a flow velocity processor 51, which maps the Doppler flow values to color values for display. The color values are applied to a scan converter and display processor 62, which spatially arranges the color values in the desired image format. The color values are displayed as pixels on a display 60, wherein each color represents a particular velocity of flow in a particular direction at that pixel location. The color flow velocity information can be overlaid with a structural image of the interior of the body utilizing the structural information provided by a 3-D B mode processor 61. This 3-D compound color image can show both the direction and velocity of blood flow, as well as the structure of the vessels or organs, which contain the flowing blood.

The Doppler system of FIG. 3 can also includes a power Doppler imaging capability. The power Doppler components include a Doppler power estimation processor 42, which estimates the Doppler signal power magnitude from the I,Q signal components at each sample volume location using the expression $(I^2+Q^2)^{1/2}$. The Doppler power estimates at each location can be processed and displayed in real time or can be averaged with earlier acquired power estimates for each sample volume location. In a preferred embodiment, each sample volume location is interrogated by a number of pulses and the estimation processor 42 utilizes the signals obtained from all interrogations in the estimations of Doppler power at the sample volume locations. These Doppler power estimates are mapped to display intensity or color values by a color power processor 52. The display values with their spatial coordinates are stored in an image sequence memory 64 and are also applied to the scan converter and display processor 62 which spatially arranges the Doppler power display values in the desired image format. The two dimensional Doppler power images may then be displayed on a display 60 or recalled from the image sequence memory 64 for three dimensional processing using a peak detector 63 for maximum Doppler power intensity detection.

User operation of the system of FIG. 3 is effected through various user controls 65 which enable the user to select the type of imaging to be performed, i.e. B mode, Doppler color flow velocity imaging or Doppler color power imaging, and to store and retrieve images from the image sequence memory 64 for three dimensional display, for example.

Referring to FIG. 1, the tissue/flow separation processor 30 comprises means for ultrasound signal whitening. According to the invention:

when a target receives one emission beam, then said target is examined using four receive beams to sixteen receive beams in parallel;

an ensemble length of three to four successive transmissions performed along a transmission beam direction allows analyzing the temporal variations of the successive signals due to displacement of the target;

the receive beams of such a same multiline ensemble see the same target differently, i. e. they see the same flow and tissue Doppler components with different perspective;

the beam signals of flow echoes and the beam signals of tissue echoes are substantially temporally uncorrelated, but they are spatially correlated;

the beam signals of the flow echoes and the beam signals of the tissue echoes form unknown linear combinations.

According to the invention, a new linear combination is provided for the tissue information signals on the one hand and for the fluid flow information signals on the other hand, such that the resulting signals of flow echoes and the resulting signals of tissue echoes are temporally uncorrelated. The technique, which is used according to the invention for providing the linear combinations, is called hereafter a "multiline data whitening" technique or "ultrasound signal whitening" technique. Hence the technique of the invention implies simple computations that can be performed in real time.

According to the invention, it is possible to extract flow signals with only one ensemble length of three, four or more from spatial combination of ultrasound signals. The means of the invention for "ultrasound signal whitening", which is applied to 3-D color flow imaging, allows the separation of the temporally uncorrelated Doppler signal components corresponding to flow Doppler signals and tissue Doppler signals. The correlation matrix of the multiline Doppler signal set is first calculated. This matrix is diagonalized. This permits of computing a spatial correlation diagonal matrix allowing the separation of the temporally uncorrelated Doppler components corresponding to flow signals and tissue signals. The diagonal matrix is denoted by D. And the eigen vectors matrix is denoted by E. The number of temporal samples or number of successive transmissions, which can be three, four or more, is denoted by N.

For each insonification depth of the volume, these definitions lead to the following formulations in the case of two beams, denoted by Beam 1 and Beam 2.

Beam 1 $X_1(T)=A_{1,flow}S_{flow}(T)+A_{1,tissue}S_{tissue}(T)$

Beam 2 $X_2(T)=A_{2,flow}S_{flow}(T)+A_{2,tissue}S_{tissue}(T)$

This formulation can be extended to a larger number N of beams. In these formulations, T=1 to N.

Since tissue and flow signals are temporally uncorrelated, two linear combinations of ($X_1$, $X_2$) must be found comprising a linear combination $Z_1(T)$ for the flow, and a linear combination $Z_2(T)$ for the tissue, leading to:

Flow $Z_1(T)=W_{11}X_1(T)+W_{12}X_2(T)$

Tissue $Z_2(T)=W_{21}X_1(T)+W_{22}X_2(T)$

With $[Z_1*Z*_2]=0$ $[Z_1*Z*_2]=0$ $[Z_1*Z*_2]=1$ $[Z_2*Z*_2]=1$ and $C_Z=I$

Hereafter, the Flow and Tissue signals are called "Sources". The Sources are independent. Since neither the Sources nor the Combinations are known, the further problem to solve is a "Blind Source Separation" problem. However, the Sources S formed by Tissue and Flow Signals, are temporally uncorrelated, but spatially correlated. Hence, the Source Separation Resolution leads to find W verifying:

$Z=WX=S$

With the condition:

$C_Z=ZZ^{*T}=I$. The solution is:

$W=D^{-1/2}E^{*T}$ $C_X=XX^{*T}=EDE$

With $ZZ^{*T}=WC_XW^{*T}=D^{-1/2}E^{*T}EDE^{*T}ED^{-1/2}=I$

Where E=orthonormal eigen vectors matrix of $C_X$, and D=eigen values diagonal matrix of $C_X$.

These calculations are simplified in the case when two beams are considered. In this case, the correlation matrix is the cross-correlation of Doppler signals between beam signals for each insonification depth. A two beams system creates a 2×2 matrix:

$$C_{X1,1} = \sum_{T=1}^{N} X_1(T) * \breve{X}_1(T)$$

$$C_{X2,2} = \sum_{T=1}^{N} X_2(T) * \breve{X}_2(T)$$

$$C_{X1,2} = \sum_{T=1}^{N} X_1(T) * \breve{X}_2(T)$$

In case of normalized signals:

$Y_1 = X_1/\|X_1\|$ $Y_2 = X2/\|X2\|$ $$C = \sum_{T=1}^{N} Y_1(T) * \breve{Y}_2(T)$$

$$CN_x = \begin{pmatrix} 1 & C \\ C^* & 1 \end{pmatrix}$$

$\lambda = 1 \pm \sqrt{C*C^*} = 1 \pm \|C\|$

-continued $$E_\pm = 1/\sqrt{2} \begin{vmatrix} e^{j\phi} \\ \pm e^{-j\phi} \end{vmatrix} \text{ with } \phi = \arg(C)/2$$

$$E = E^{*T} = 1/\sqrt{2} \begin{pmatrix} e^{j\phi} & e^{j\phi} \\ e^{-j\phi} & -e^{-j\phi} \end{pmatrix}$$

Figure 4A:
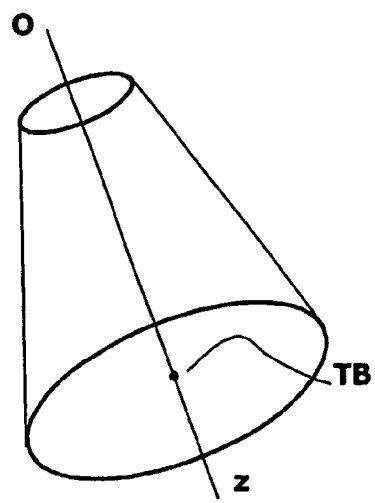
FIG. 4A shows an example of transmit beam geometry.
Figure 4B:
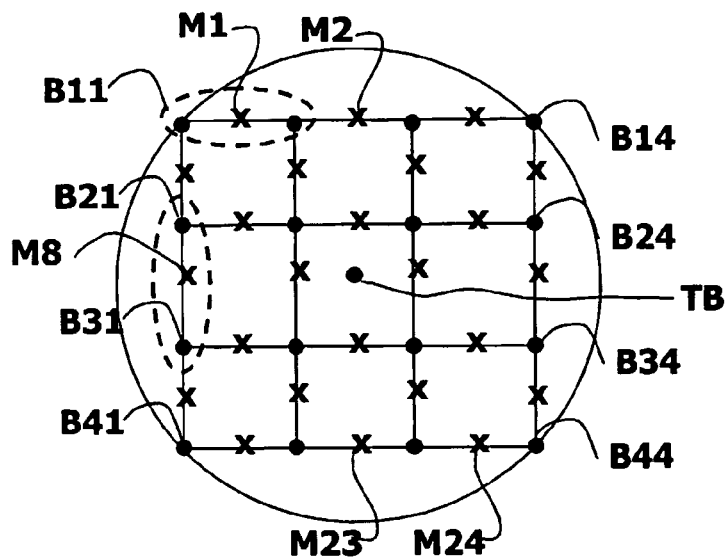
FIG. 4B shows an example of receive beam geometry with respect to the transmit beam geometry with corresponding possible positions of motion estimations and FIG. 4C shows other possible positions of motion estimations.
Figure 4C:
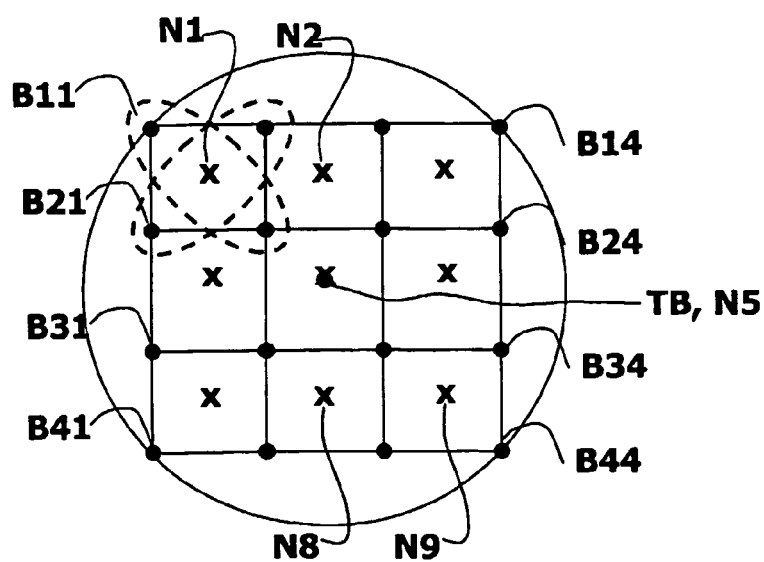

Referring to FIG. 4A, 4B and 4C, a very important application of this two beams resolution is described. This two beams resolution may be used with any order of multiline. FIG. 4A represents one transmitted beam of direction Oz and center TB. Referring to FIG. 3B, to said transmit beam correspond for instance sixteen receive beams. The centers of the receive beams are represented respectively by:

B11, B12, B13, B14,
B21, B22, B23, B24,
B31, B32, B33, B34,
B41, B42, B43, B44.

Indeed, with sixteen receive beams acquired simultaneously, the data may be simultaneously processed by couple of two receive beams in order to maintain a good spatial resolution of the resulting 3-D data. With sixteen receive beams acquired with a square scheme, B11, B12, B13, B14, ... B34, B44, as illustrated by FIG. 3B, one can form couples such as, for example:

(B11, B12) that will provide one spatial motion estimation at the position M1, (B21, B31) that will provide another spatial motion estimation at the position M8, and so on, so that with sixteen beams, twenty four spatial motion estimations M1 to M24 may be achieved. Besides, four (2×2) beams forming quadruplets, such as (B11,B12,B21,B22), may be used to estimate nine spatial motion estimations at positions N1 to N9, as illustrated by FIG. 4C.

Twenty-four spatial motion estimations provided by associating the beams in couples, and nine spatial motion estimations provided by associating the beams in quadruplets give thirty-three possible estimated points M and N.

Figure 2:
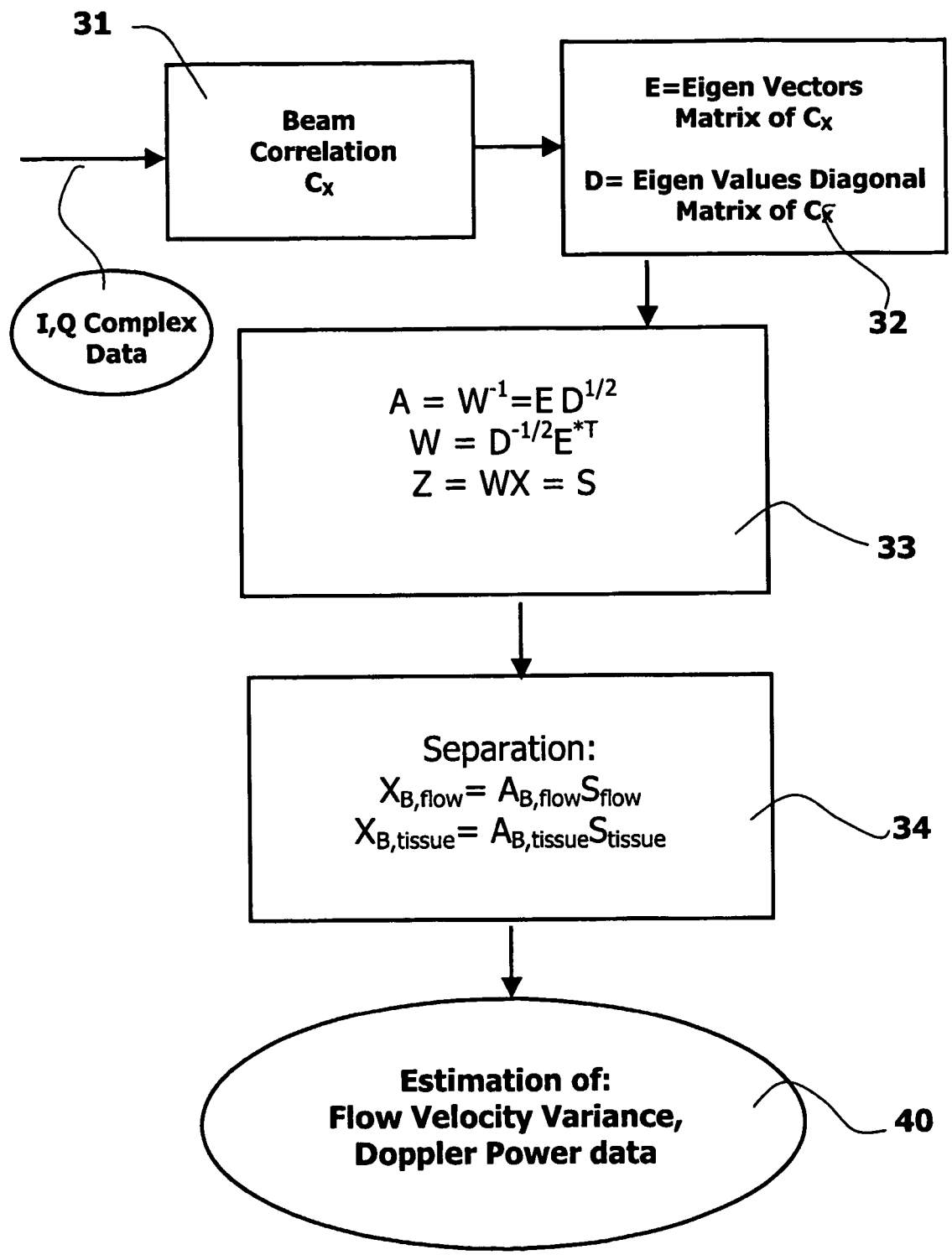
FIG. 2 represents a detailed block diagram of the ultrasonic imaging system of FIG. 1.

FIG. 2 is a block diagram that illustrates the Source Separation Algorithm of the technique of the invention. According to this technique, in a step 31 the beam correlation matrix Cx is calculated. Then the eigen vectors matrix E and matrix D are calculated in step 32. The signal S is calculated in step 33. Then separation is operated in step 34. The result further permits estimation of Doppler power data and Doppler flow velocity data.

The Doppler signals are further processed classically with classical autocorrelation algorithms using processor 40, as described above.

The invention claimed is:

1. An ultrasound phased array imaging system comprising:
   a probe with a 2-D array of transducer elements for acquiring 3-D ultrasound data of a volume of a body, including moving tissue and fluid flow;
   a beamforming system for emitting and receiving in real time ultrasound beams in said volume, which acquires, in real time and in 3-D, more than one spatial receive beams signals for each transmission beam within an ensemble length of more than two temporal samples, among which the receive flow beam signals and the receive tissue beam signals are substantially temporally uncorrelated but spatially correlated;
   separation means comprising adaptive spatial tissue filtering means, using simultaneously more than one spatial receive beam signals acquired in 3-D within the ensemble length of more than two temporal samples, for analyzing temporal variations of the respective successive receive signals and for extracting flow receive beam signals from spatial combinations of receive beam signals;
   processing means and display means for processing flow Doppler signals and for displaying images based on said processed flow Doppler signals.

2. The ultrasound phased array imaging system of claim 1, wherein the filtering means comprises calculations means for:
   calculating an autocorrelation function of temporally uncorrelated and spatially correlated tissue and flow receive signals,
   calculating a spatial correlation diagonal matrix from said autocorrelation function, and
   separating the temporally uncorrelated Doppler components corresponding to flow and tissue signals from said diagonal matrix.

3. The ultrasound phased array imaging system of claim 1, wherein the filtering means extracts the receive flow Doppler signals from spatial combination of receive beam signals using simultaneously four to sixteen or more spatial receive beam signals acquired in 3-D within an ensemble length of three, four or more temporal samples.

4. The ultrasound phased array imaging system of claim 1, wherein, in order to enhance spatial resolution of the extracted 3-D receive flow Doppler signals, receive beams signals are simultaneously acquired corresponding to receive beams formed according to a regular scheme and are simultaneously processed by couples corresponding to two adjacent receive beams, or by sets corresponding to several grouped receive beams, to provide supplementary spatial motion estimations at spatial positions between the beams of the couples or at the centers of the grouped beams.

5. The ultrasound phased array imaging system of claim 1, wherein, in order to enhance resolution of the extracted 3-D receive flow Doppler signals, sixteen receive beams signals are simultaneously acquired, corresponding to receive beams disposed according to a square scheme, and are simultaneously processed:
   by couples of receive beam signals corresponding to two adjacent receive beams, forming twentyfour couples, to provide twentyfour spatial motion estimations (M1-M24), respectively at twentyfour spatial positions between the beams of the couples; and/or
   by quadruplets of receive beam signals corresponding to four (2×2) receive beams forming a square, forming nine quadruplets to provide nine spatial motion estimations (N1-N9), respectively at spatial positions at the center of the squares formed by the beams of the quadruplets; for providing nine to thirtythree supplementary motion estimations to the sixteen motion estimations.

6. The ultrasound phased array imaging system of claim 1, comprising:
   demodulation means, which computes complex data signals (4×I, Q) from each of four to sixteen or more receive beam signals;
   separation means, which separates complex data signals of moving tissue from complex data signals of fluid flow, using an ensemble length of at least three successive transmissions along an emission beam direction to analyze temporal variations of the respective successive receive signals;

processing means for processing the extracted complex data signals of fluid flow to provide fluid flow information data;

and display means to process fluid flow information data and to display images based on said processed fluid flow information data.

7. The ultrasound phased array imaging system of claim 6, wherein the processing means comprises:

a Doppler shift estimate for estimating Doppler velocity from the extracted complex data signals of fluid flow;

a color flow velocity processor for mapping flow velocity values on color values;

and/or:

a Doppler power estimate for estimating Doppler power magnitude from the extracted complex data signals of fluid flow;

a color power processor for mapping the estimated power magnitude on color values.

8. The ultrasound phased array imaging system of claim 6, comprising:

a B mode processor for processing the amplitude information of the echo signals, on a spatial basis, for the formation of structural images of the tissue.

9. The ultrasound phased array imaging system of claim 6, comprising:

a display processor for processing the B mode data, color flow velocity data, color power data, and an image memory for memorizing the image data for display; and a user control for the user to select the images to display in one mode or in combined modes.

10. An ultrasound imaging method comprising steps of:

acquiring 3-D ultrasound data of a volume of a body, including moving tissue and fluid flow;

emitting and receiving ultrasound beams in said volume, comprising acquiring, in real time and in 3-D, more than one spatial receive beams signals for each transmission beam within an ensemble length of more than two temporal samples, among which the receive flow beam signals and the receive tissue beam signals are substantially temporally uncorrelated but spatially correlated;

separating receive flow Doppler signals means from receive tissue Doppler signals with adaptive spatial tissue filtering, using simultaneously more than one spatial receive beam signals acquired in 3-D within the ensemble length of more than two temporal samples, for analyzing temporal variations of the respective successive receive signals and for extracting flow receive beam signals from spatial combinations of receive beam signals; and processing flow Doppler signals and displaying images based on said processed flow Doppler signals.

11. The ultrasound imaging method of claim 10, further comprising the steps of:

calculating an autocorrelation function of temporally uncorrelated and spatially correlated tissue and flow receive signals, calculating a spatial correlation diagonal matrix from said autocorrelation function, and separating the temporally uncorrelated Doppler components corresponding to flow and tissue signals from said diagonal matrix.

12. The ultrasound imaging method of claim 10, further comprising the steps of:

simultaneously acquiring receive beams signals corresponding to receive beams formed in a regular scheme;

simultaneously processing said signals by couples corresponding to two adjacent receive beams, or by groups corresponding to several receive beams, to provide supplementary spatial motion estimations at spatial positions between the beams of the couples or at the centers of the groups.

* * * * *